(12) United States Patent
Paul

(10) Patent No.: US 9,063,074 B2
(45) Date of Patent: Jun. 23, 2015

(54) ANALYZING TISSUE MORPHOLOGY IN THREE DIMENSIONS

(75) Inventor: Manibrata Paul, Kolkata (IN)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 804 days.

(21) Appl. No.: 13/202,269

(22) PCT Filed: Feb. 14, 2011

(86) PCT No.: PCT/IB2011/000266
§ 371 (c)(1),
(2), (4) Date: Aug. 18, 2011

(87) PCT Pub. No.: WO2012/090035
PCT Pub. Date: Jul. 5, 2012

(65) Prior Publication Data
US 2012/0170022 A1    Jul. 5, 2012

(30) Foreign Application Priority Data

Dec. 30, 2010    (IN) .............................. 3168/DEL/2010

(51) Int. Cl.
*G01N 21/359* (2014.01)
*G01N 21/31* (2006.01)

(52) U.S. Cl.
CPC .............. *G01N 21/31* (2013.01); *G01N 21/359* (2013.01)

(58) Field of Classification Search
CPC .......................... G01N 24/087; G01N 21/359
USPC ........ 250/338.1, 458.1, 336.1, 339.12, 341.2; 356/303; 600/310, 442
See application file for complete search history.

(56) References Cited

U.S. PATENT DOCUMENTS

| | | | | |
|---|---|---|---|---|
| 5,676,142 A * | 10/1997 | Miwa et al. | .................... | 600/310 |
| 5,692,504 A * | 12/1997 | Essenpreis et al. | ........... | 600/316 |
| 5,752,519 A * | 5/1998 | Benaron et al. | ................ | 600/476 |
| 5,803,909 A * | 9/1998 | Maki et al. | .................... | 600/310 |
| 5,807,261 A * | 9/1998 | Benaron et al. | ................ | 600/473 |
| 6,201,989 B1 * | 3/2001 | Whitehead et al. | ........... | 600/476 |
| 6,341,036 B1 * | 1/2002 | Tearney et al. | ................ | 359/368 |

(Continued)

FOREIGN PATENT DOCUMENTS

| WO | WO 00/25112 | 5/2000 |
|---|---|---|
| WO | WO 02/41760 | 5/2002 |
| WO | WO 2008/110974 | 9/2008 |

OTHER PUBLICATIONS

Infrared Spectroscopy of Human Tissue. I. Differentiation and Maturation of Epithelial Cells in the Human Cervix, L. Chiriboga et al., Biospectroscopy, vol. 4, 47-53 (1998).

(Continued)

*Primary Examiner* — David Porta
*Assistant Examiner* — Djura Malevic
(74) *Attorney, Agent, or Firm* — Foley & Lardner LLP

(57) ABSTRACT

Light is introduced into a tissue sample. The resulting light that passes through the tissue sample may be spectrally analyzed to determine its intensity at a number of frequencies. From these intensities, a chemical nature of the tissue sample may be determined. By performing this process one or more times, a three-dimensional representation of the morphology of the tissue sample can be developed, and this representation may be used to determine whether the tissue sample is healthy or abnormal.

18 Claims, 5 Drawing Sheets

(56) References Cited

U.S. PATENT DOCUMENTS

| | | | |
|---|---|---|---|
| 6,556,853 B1* | 4/2003 | Cabib et al. | 600/407 |
| 7,016,717 B2 | 3/2006 | Demos et al. | |
| 7,231,243 B2* | 6/2007 | Tearney et al. | 600/407 |
| 7,285,790 B2* | 10/2007 | Tanaka et al. | 250/458.1 |
| 7,505,811 B2* | 3/2009 | Hashimshony | 600/547 |
| 8,032,200 B2* | 10/2011 | Tearney et al. | 600/407 |
| 2002/0122246 A1* | 9/2002 | Tearney et al. | 359/368 |
| 2006/0173359 A1* | 8/2006 | Lin et al. | 600/478 |
| 2009/0103792 A1 | 4/2009 | Rahn et al. | |
| 2009/0137908 A1 | 5/2009 | Patwardhan | |
| 2009/0270702 A1* | 10/2009 | Zeng et al. | 600/323 |
| 2010/0198081 A1* | 8/2010 | Hanlin et al. | 600/478 |
| 2011/0159562 A1* | 6/2011 | Deisseroth et al. | 435/173.8 |

OTHER PUBLICATIONS

Fourier Transform Infrared Imaging Spectroscopic Analysis of Tissue Engineered Cartilage: Histologic and Biochemical Correlations, Kim et al., Journal of Biomedical Optics, May-Jun. 2005; 10(3):031105.

Femtosecond High Resolution Near Infrared Non-linear Optical Imaging (NIR-NLOI): Applications in Cell and Tissue Engineering, Tirlapur et al., European Cells and Materials vol. 11. Suppl. 3, 2006 (p. 22).

Infrared Micro-Spectral Imaging: Distinction of Tissue Types in Axillary Lymph Node Histology, Bird et al., BMC Clinical Pathology 2008, 8:8.

Visualization of Photon Propagation and Abnormality Detection, Ge et al., Optical Biopsy III, Proceedings of SPIE vol. 3917 (2000), p. 204-p. 211.

Infrared Tissue Imaging Applications Growing in Biomedical Research and Diagnosis by Sharon Williams [online], Feb. 1, 2006 [retrieved on Aug. 2, 2011]. Retrieved from the Internet:<URL: http://license.icopyright.net/user/viewFreeUse.act?fuid=MTM2MDg2Nzc%3D>.

International Search Report and Written Opinion prepared by the Australian Patent Office for PCT/IB2011/000266 completed Apr. 29, 2011.

"Olympus FluoView Resource Center: Confocal Gallery—Human Skin Tissue," accessed at http://web.archive.org/web/20090323073903/http://www.olympusfluoview.com/gallery/humanskinirdicsmall.html, accessed on Oct. 30, 2014, p. 1.

* cited by examiner

ANALYZING TISSUE MORPHOLOGY IN THREE DIMENSIONS

BACKGROUND

Embryonic and adult stem cells have the potential to grow and diversify into various types of specialized cells. Thus, these cells may be able to be used for tissue re-growth or replacement. However, such engineered tissue often fails to develop properly in vitro or after being transplanted, as it may be subject to tumors, such as teratomas, that can grow encapsulated within the tissue.

CROSS-REFERENCE TO RELATED APPLICATION

The present application claims priority to Indian patent application serial number 3168/DEL/2010, filed on Dec. 30, 2010, the entire contents of which are incorporated by reference. This present application is a U.S. National Phase Application pursuant to 35 U.S.C. §371 of International Application No. PCT/IB2011/000266 filed Feb. 14, 2011, the entire contents of which are incorporated by reference.

SUMMARY

In example embodiments, devices and methods for analyzing tissue morphology in three dimensions are presented. Light may be passed through one or more three-dimensional locations in a tissue sample. The light may be substantially in the infrared (IR) or near-infrared (NIR) range. A device receiving this light may focus, collimate and analyze the spectral characteristics of the light to determine a chemical nature of the tissue sample at the three-dimensional location. This chemical nature may include a chemical structure of the tissue sample, and may also reflect a morphology of the tissue sample.

The light may emanate from any light source, such as a laser or a light emitting diode (LED). A light receptor may receive the light and focus it so that a collimator can parallelize the light for analysis. An analyzer may receive the parallelized light and perform a spectral analysis on this light.

If the light source produces polychromatic light, the spectral analysis may include diffusing the parallelized light into multiple spectral components, and measuring the respective intensity of each spectral component. Some of this measurement may occur via a computing device. If the light source produces monochromatic light, monochromatic light of various frequencies may be passed through the tissue sample to determine the spectral absorption patterns of the tissue sample.

Additionally, the relative positioning of the light source and the tissue sample may be adjusted to direct the light into different three-dimensional locations in the tissue sample. For example, the angle of incidence of the light to the tissue sample may be modified, and the focus of the light within the tissue sample may be altered. As a result, multiple three-dimensional locations in the tissue sample can be subjected to multiple frequencies of light in order to determine, in a non-invasive fashion, whether the tissue sample is healthy.

The foregoing summary is illustrative only and is not intended to be in any way limiting. In addition to the illustrative aspects, embodiments, and features described above, further aspects, embodiments, and features will become apparent by reference to the figures and the following detailed description.

DETAILED DESCRIPTION

Figure 1:
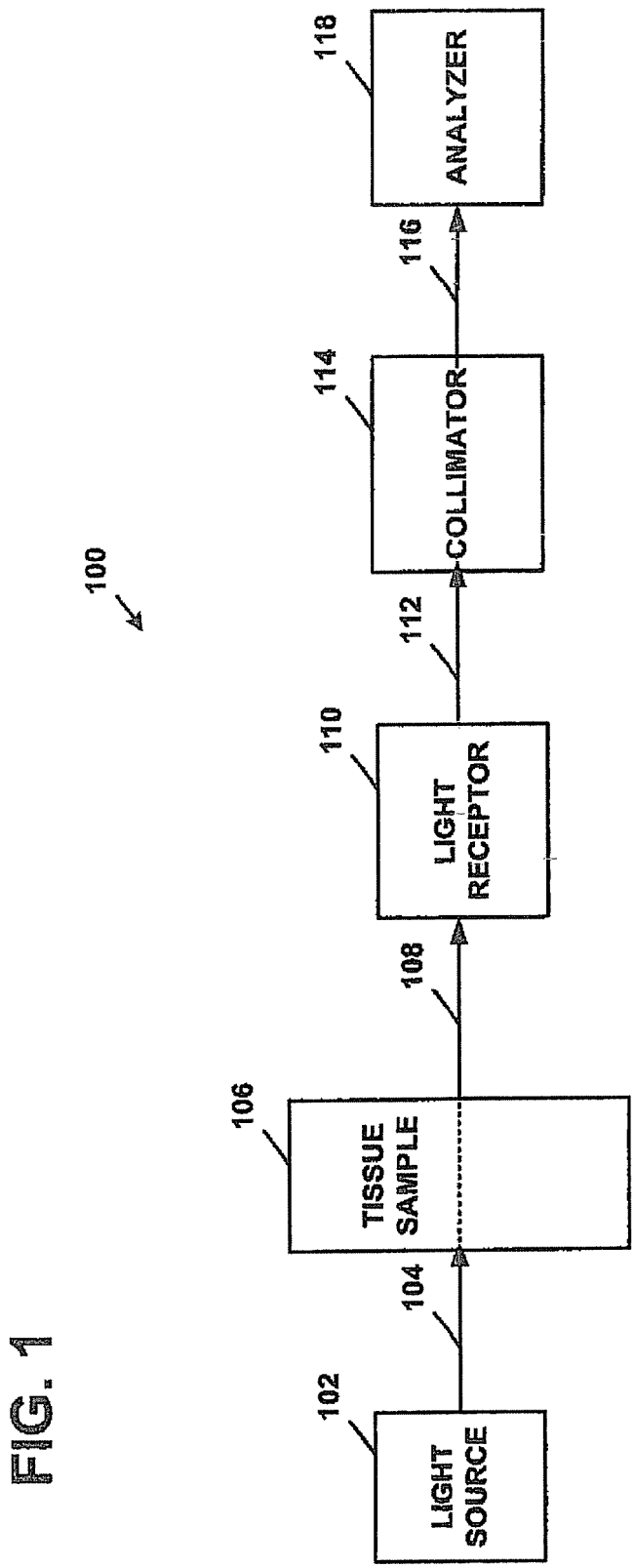
FIG. 1 is a depiction of a device or devices for passing light through a location in a tissue sample, in accordance with an example embodiment.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Molecules making up many forms of biological tissue tend to absorb specific frequencies of light. The frequencies that a given tissue sample absorbs may depend on the chemical nature of the tissue. For example, a molecule with a chemical bond that vibrates at a particular frequency may absorb light with a corresponding frequency. Therefore, by passing light through a tissue sample and analyzing the intensity of the resulting light at various frequencies, the type of chemical bonds in the tissue sample can be determined. These types of chemical bonds can, in turn, be used for example to determine whether the tissue is healthy or defective.

The chemical content of healthy tissue and unhealthy tissue may be different. For some types of tissue malignancy, the nucleus of the cell increases and the nucleus-to-cytoplasm (N:C) ratio also increases. In such tissue, there may be more nuclear material than cytoplasmic material compared to normal cells. As the nucleus and the cytoplasm of the cell are composed of different elements and compounds, the spectral characteristics of these sections of a cell are likely to be different. Thus, a cell with a malignant tumor causing the cell's nucleus to be large may exhibit different spectral characteristics than a cell that is benign.

However, performing frequency analysis on light passing through three-dimensional living tissue can be challenging. Some frequencies of light do not penetrate well through tissue. However, other frequencies of light, such as infrared (IR) and near infrared (NIR) light, can penetrate through at least some types of tissue, but are absorbed by other types of tissue. Thus, by performing a broad-spectrum analysis of the absorption characteristics of various three-dimensional locations in a tissue sample, the chemical nature of these three-dimensional locations can be determined. In this way, the cellular and chemical structure of the tissue sample can also be determined.

In order to facilitate the development of engineered tissue samples, it is desirable to be able to determine whether engineered tissue, such as embryonic stem cell tissue, is developing properly. One way of doing so is to monitor the morphology of the engineered tissue as it develops. The devices and methods described herein provide example embodiments that may determine the morphology of a tissue sample. From this determined morphology, tumors and/or other abnormalities may be detected.

FIG. 1 is a depiction 100 of a device or devices for passing light through a location in a tissue sample 106. To that end, a light source 102 may be configured to produce a light 104. Light source 102 may be a laser, a light-emitting diode, or another component capable of providing light. Further, light source 102 may be an array of light sources, each configured to provide a different frequency range of light, and/or to focus on a different location of tissue sample 106. Alternatively, light source 102 may not be the ultimate source of light 104. Instead, light source 102 may redirect or guide light 104 from another light source into tissue sample 106.

As used herein, the term "light" may refer to any frequency of electromagnetic radiation, visible or non-visible, including infrared (IR) or near-infrared (NIR) light. It should be understood that IR light typically exhibits a wavelength between about 0.7 and about 300 micrometers, while NIR light typically exhibits a wavelength between about 0.7 and about 3 micrometers. However, these wavelength ranges are not exact. Thus, IR and/or NIR light may exhibit wavelengths outside of these ranges. Additionally, the light may be polychromatic (comprising many frequencies) or monochromatic (comprising a single frequency or a limited number of frequencies).

Light 104 may pass through tissue sample 106, resulting in light 108. Due to the chemical nature of tissue sample 106, certain frequencies of light 104 may be absorbed by the molecules in tissue sample 106. As a result, light 108 may have different spectral characteristics than light 104 (e.g., the frequencies of light 104 that were absorbed by the molecules in tissue sample 106 may not be present in light 108). In particular, light 108 may produce an image representing the structure of at least part of tissue sample 106. While tissue sample molecules may be organic, this technique may be applied to non-organic molecules as well.

Light 108 may be received by a light receptor 110. Light receptor 110 may include any type of photodetector, such as but not limited to an optical sensor, a photovoltaic sensor, a charge-coupled device (CCD), a complementary metal-oxide semiconductor (CMOS) sensor, and other types of photosensitive chemical elements. As an example of a photodetector, an optical sensor may detect characteristics of light 108 by measuring, for instance, changes in the intensity or phase of light 108. These types of optical sensors may be referred to as intensity sensors or interferometric sensors, respectively.

Light receptor 110 may be configured to provide light 112 to collimator 114. In particular, light receptor 110 may include a lens to focus light 112 at collimator 114. Instead of or in addition to the lens, the light receptor 110 may use a grating, a fiber-optic cable, a prism, and/or a focal plane array to focus light 112 at collimator 114.

Collimator 114 may be configured to collimate light 112 to form light 116. In a possible embodiment, the rays of light 112 may be non-parallel (e.g., the rays of light 116 scatter or disperse as they propagate), while the rays of light 116 may be substantially parallel (e.g., the rays of light 116 scatter or disperse minimally as they propagate). Among other possible advantages, this parallel nature of light 116 may ease the spectral analysis of light 116.

To that point, light 116 may be received by analyzer 118. Analyzer 118 may be configured to perform one or more spectral analyses on light 116. An outcome of these spectral analyses may provide the intensities of the various frequencies of light 116. In a possible embodiment, analyzer 118 may perform one or more Fourier transforms and/or wavelet transforms on light 116 to determine the intensity of its component frequencies. These Fourier transforms and/or wavelet transforms may be performed by circuitry, or program instructions available to a computing device, embedded in or available to analyzer 118. In another possible embodiment, analyzer 118 may comprise a light disperser, such as a prism, or a light diffractor, such as a slit or diffraction grating. As a result of passing through the light disperser or the light diffractor, light 116 may separate into two or more beams of light, where each beam includes a different frequency range. Either of these embodiments may be combined with the other, in whole or in part, without departing from the scope of the invention.

Analyzer 118 may also comprise a focal plane array to receive the separated beams of light. A focal plane array may include a plurality of receptors, each configured to sense photons of in a particular frequency range. By arranging the light disperser or the light diffractor to aim beams of given frequencies at the appropriate receptors in a focal plane array, the focal plane array can measure the intensity of light 116 at various frequencies.

From the output of analyzer 118, the frequencies of light 104 that were absorbed, as well as those that were not absorbed, by tissue sample 106 may be determined. This output may take the form of a spectral chart that indicates the relative or absolute intensity of the light across a frequency spectrum. For instance, the spectral chart may be a two dimensional chart with an x-axis representing spectral frequency, and the y-axis representing intensity of the light. In some embodiments, the spectral chart may present the IR or NIR spectrum divided into bins of wavelength ranges.

For IR light, a possible arrangement of these bins could be from about 0.7-10.0 micrometers, from about 10.0 to 20.0 micrometers, from about 20.0 to 30.0 micrometers, and so on. For NIR light, a possible arrangement of these bins could be from about 0.7-1.0 micrometers, from about 1.0 to 1.4 micrometers, from about 1.4 to 1.8 micrometers, from about 1.8 to 2.2 micrometers, from about 2.2 to 2.6 micrometers, and from about 2.6 to 3.0 micrometers. For each bin, the spectral chart may provide a degree of intensity that the light exhibits in the bin's wavelength ranges. It should be understood that the intensity of light can be determined in a number of ways, and that the scope of the embodiments are not limited to the way in which the intensity is measured. Thus, the intensity could be, for instance, a measure of radiance, or luminescence of the light. Additionally, it should also be understood that more or fewer wavelength bins, or wavelength bins of a different size, may be used.

Regardless of the configuration of analyzer 118, light may be introduced to tissue sample 106 at two or more different frequencies in order to facilitate the building of a spectral chart. Thus, a wide-band, multi-spectral, or hyper-spectral analysis, through various ranges of IR, NIR, or other types of light, may be used to provide multiple samples for the spectral chart.

In order to develop the spectral chart, light may be aimed at different three-dimensional locations within a tissue sample. While usually just the exposed surface of any tissue is visible, most tissues, organs, and biological structures are three-dimensional. When a tissue, organ, or biological structure contains a tumor, this tumor may be on the surface of the tissue, organ, or biological structure. But, if the tumor is below the surface of the tissue, organ, or biological structure, it may be difficult to detect the tumor without analyzing the tissue, organ, or biological structure in three dimensions.

Whether the output of analyzer 118 takes the form of a spectral chart or some other arrangement, this output may be used to determine the composition of the tissue sample. The molecules in many forms of tissue oscillate at one or more vibrational frequencies. One way to determine the characteristics of these vibrations is IR spectroscopy. In particular, the energy used to change vibrational states may correspond to IR frequencies. Thus, chemical bonds that hold molecules together may absorb IR light of specific frequencies. For instance, a C—H (carbon-hydrogen) bond absorbs light at a shorter wavelength than a C—C (carbon-carbon) bond. As a result, the chemical nature of specific locations within a tissue sample can be determined according to the embodiments herein.

Based on the determined chemical nature of the tissue sample, the morphology or function of the tissue sample may also be established. Therefore, tumors, abnormalities, or malignancies in the tissue sample may be detected at an early phase of development, and these potential problems may be able to be addressed before the entire tissue sample is damaged.

Although a number of discrete components are depicted in FIG. 1, more or fewer components may be used. For instance, light receptor 110, collimator 114, and analyzer 118 may be combined into a single device. Additionally, any of the components in FIG. 1 may be further divided into sub-components.

Figure 2:
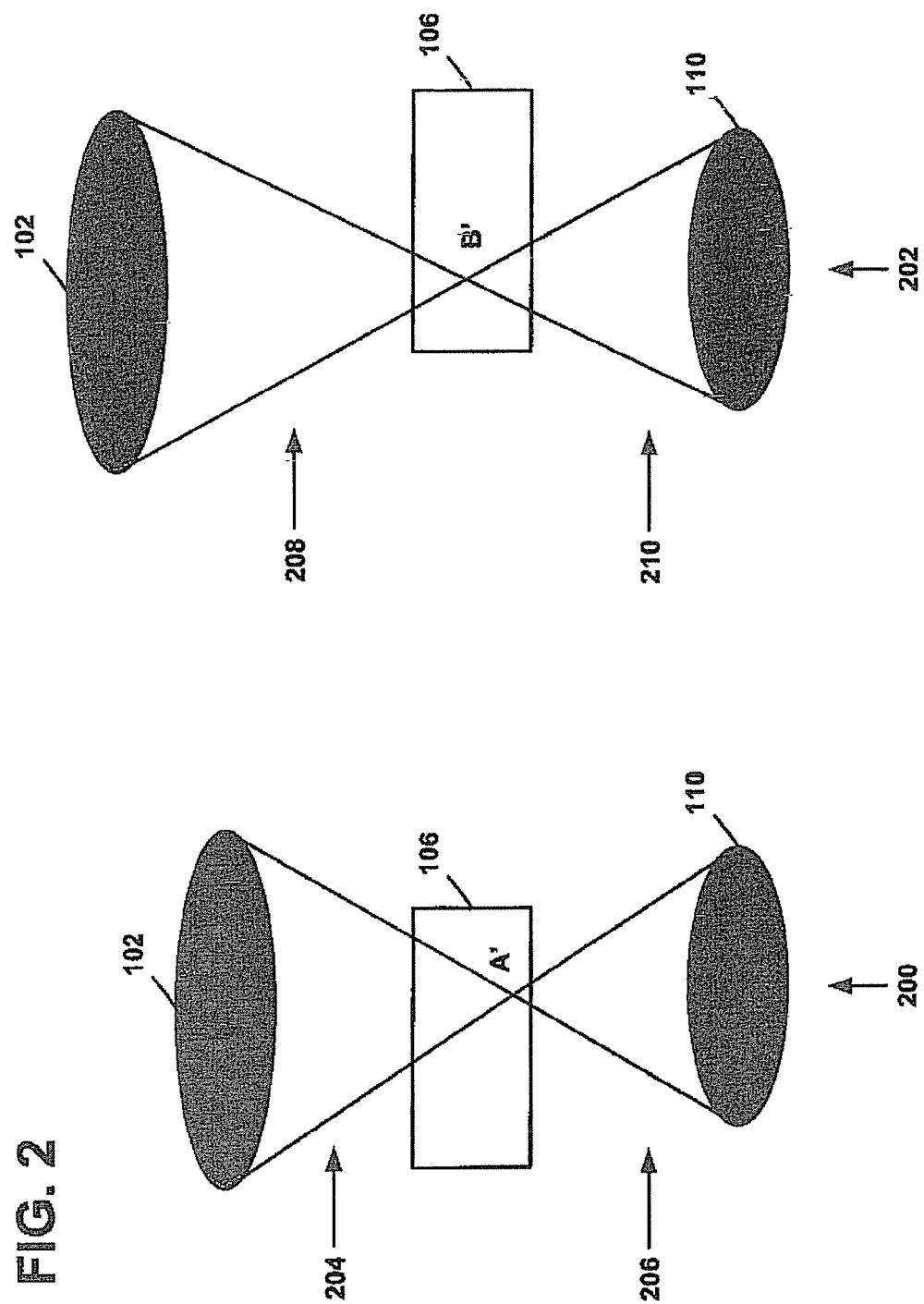
FIG. 2 is a depiction of a device or devices for aiming light at a three-dimensional location in a tissue sample, in accordance with an example embodiment.

FIG. 2 is a depiction of a device or devices for aiming light at a three-dimensional location in a tissue sample, in accordance with an example embodiment. In configuration 200, light 204 may be transmitted through location A' of tissue sample 106 by or via light source 102. Light source 102 may be wide so that the intensity of light 204 is not significant in the optical path between light source 102 and light receptor 110, except for focal point A'. This arrangement may be adjusted so that, in configuration 202, the intensity of light 208 is not significant in the optical path between light source 102 and light receptor 210, except for focal point B'.

Light 206 may emerge from tissue sample 106 and may be received by light receptor 110. Similarly, light 208 may be transmitted through location B' of tissue sample 106, also by or via light source 102. Light 210 may emerge from tissue sample 106 and may also be received by light receptor 110. The received light in either or both of configurations 200 and 202 may be spectrally analyzed. Thus, by aiming light at one or more three-dimensional locations, such as focal points A' and B', a representation of the morphology of the tissue sample can be produced.

Considering configuration 200, one way in which light 204 can be aimed at a particular three-dimensional location is via changing the angle of incidence between light 204 and tissue sample 106. This, in turn, may influence the direction at which the light travels through tissue sample 106. Additional ways in which light 204 can be aimed at a particular three-dimensional location include, but are not limited to, adjusting the distance between light source 102 and tissue sample 106, and/or adjusting the focus of light 204 into tissue sample 106. Adjusting the focus of light 204 may be facilitated if light source 102 comprises a lens that can direct light to a Particular point in tissue sample 106.

Figure 3:
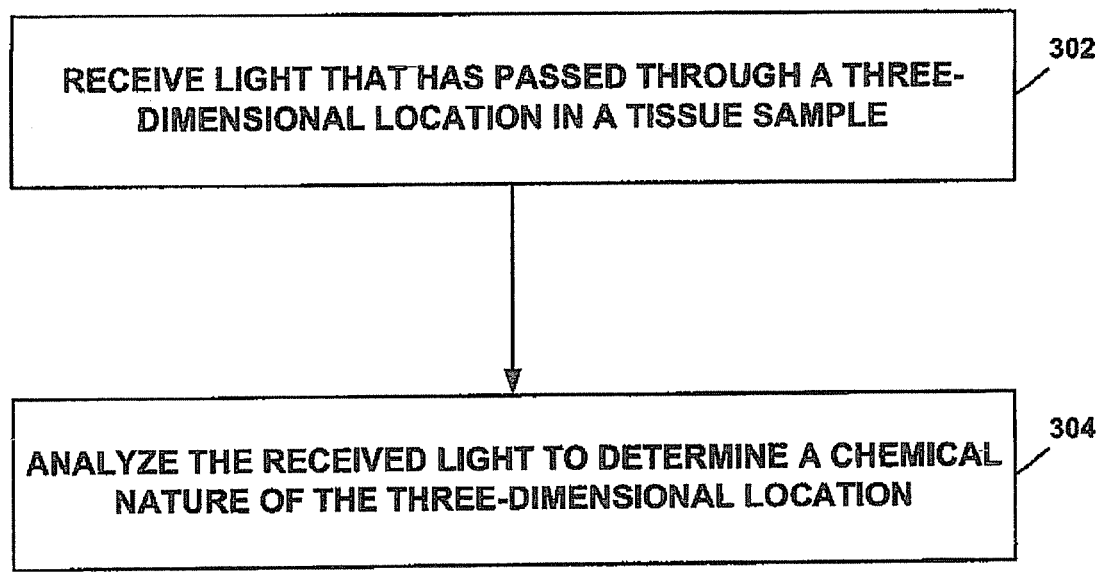
FIG. 3 is a flow chart, in accordance with an example embodiment.

FIG. 3 is a flow chart, in accordance with an example embodiment. At step 302, light that has passed through a first three-dimensional location in a tissue sample is received. The light may be substantially IR or substantially NIR. Further, the light may be substantially monochromatic or substantially polychromatic. The tissue sample may be, for example, derived from embryonic stem cells, and a goal of the analysis may be to determine whether there is a tumor in the tissue sample.

At step 304, the received light is analyzed to determine a first chemical nature of the first three-dimensional location. The analysis may involve performing a spectral analysis of the directed light. Additionally or alternatively, the analysis may involve diffusing the directed light into a plurality of spectral components and measuring the respective intensity of each spectral component in the plurality.

The light may be directed into the three-dimensional location by a-light source. Thus, the relative positioning of the light source and the tissue sample may change to direct the light to a second three-dimensional location in the tissue sample. For instance, the light source, the tissue sample, or both may be moved. Alternatively or additionally, the focus of the light source may be changed to direct the light to one or more three-dimensional locations within the tissue sample. Then, the directed light that passes through the second three-dimensional location may be analyzed to determine a second chemical nature of the second three-dimensional location.

If the light source produces polychromatic light, the spectral analysis may include diffusing the collimated light into multiple spectral components, and measuring the respective intensities of each spectral component. If the light source produces monochromatic light, the monochromatic light of various frequencies may be passed through the tissue sample to determine the spectral absorption patterns of the tissue sample.

The first chemical nature or the second chemical nature may include the respective chemical structures of the first three-dimensional location and the second three-dimensional location. Thus, based on the first chemical nature or the second chemical nature, the morphology of at least part of the tissue sample may be determined. Consequently, by directing light into and through the tissue sample, one may be able to determine whether the tissue sample is healthy, or contains a tumor or some other irregularity.

For example, the first chemical nature may be indicative of the first three dimensional location containing healthy tissue, while the second chemical nature may be indicative of the second three-dimensional location containing a tumor. By determining the chemical nature of two or more locations in this way, the position, size, and composition of the tumor may also be determined.

Figure 4:
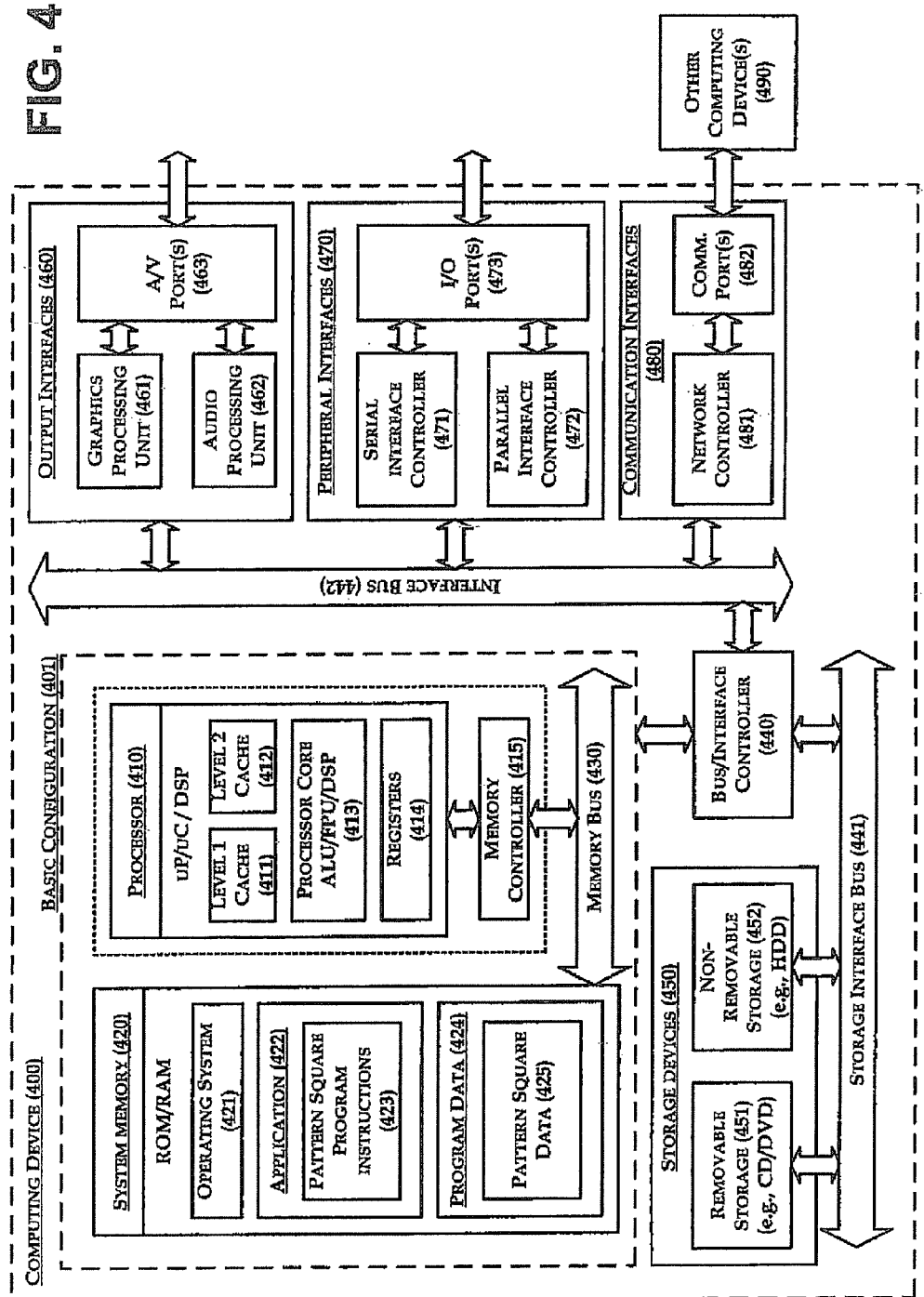
FIG. 4 is an illustrative diagram of a computing device, in accordance with an example embodiment.

FIG. 4 is a block diagram illustrating an example computing device 400 that is arranged for performing spectral analysis, or other functions, in accordance with the present disclosure. In a very basic configuration 401, computing device 400 typically includes one or more processors 410 and system memory 420. A memory bus 430 can be used for communicating between the processor 410 and the system memory 420.

Depending on the desired configuration, processor 410 can be of any type including but not limited to a microprocessor (μP), a microcontroller (μC), a digital signal processor (DSP), or any combination thereof. Processor 410 can include one more levels of caching, such as a level one cache 411 and a level two cache 412, a processor core 413, and registers 414. The processor core 413 can include an arithmetic logic unit (ALU), a floating point unit (FPU), a digital signal processing core (DSP Core), or any combination thereof. A memory controller 415 can also be used with the processor 410, or in some implementations the memory controller 415 can be an internal part of the processor 410.

Depending on the desired configuration, the system memory 420 can be of any type including but not limited to volatile memory (such as RAM), non-volatile memory (such as ROM, flash memory, etc.) or any combination thereof. System memory 420 typically includes an operating system 421, one or more applications 422, and program data 424. Application 422 includes program instructions 423 that are capable of carrying out one or more of the methods, processes, and/or functions described herein.

Program data 424 includes data 425 that may be useful for carrying out one or more of the methods, processes, and/or functions described herein. In some example embodiments, application 422 can be arranged to operate with program data 424 on an operating system 421 such that computing device 400 performs at least some of the functions described herein. This described basic configuration is illustrated in FIG. 4 by those components within dashed line 401.

Computing device 400 can have additional features or functionality, and additional interfaces to facilitate communication between the basic configuration 401 and any required devices and interfaces. For example, a bus/interface controller 440 can be used to facilitate communication between the basic configuration 401 and one or more data storage devices 450 via a storage interface bus 441. The data storage devices 450 can be removable storage devices 451, non-removable storage devices 452, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media can include volatile and nonvolatile, removable and non-removable media implemented in any method or technology for storage of information, such as computer readable instructions, data structures, program modules, or other data.

System memory 420, removable storage 451 and non-removable storage 452 are all examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 400. Any such computer storage media can be part of computing device 400.

Computing device 400 can also include an interface bus 442 for facilitating communication from various interface devices (e.g., output interfaces, peripheral interfaces, and communication interfaces) to the basic configuration 401 via the bus/interface controller 410. Example output interfaces 460 include a graphics processing unit 461 and an audio processing unit 462, which can be configured to communicate to various external devices such as a display or speakers via one or more A/V ports 463. Example peripheral interfaces 460 include a serial interface controller 471 or a parallel interface controller 472, which can be configured to communicate with external devices such as input devices (e.g., keyboard, mouse, pen, voice input device, touch input device, etc.) or other peripheral devices (e.g., printer, scanner, etc.) via one or more I/O ports 473. An example communication interface 480 includes a network controller 481, which can be arranged to facilitate communication with one or more other computing devices 490 over a network communication via one or more communication ports 482. The communication connection is one example of a communication media. Communication media may typically be embodied by computer readable instructions, data structures, program modules, or other data in a modulated data signal, such as a carrier wave or other transport mechanism, and includes any information delivery media. A "modulated data signal" can be a signal that has one or more of its characteristics set or changed in such a manner as to encode information in the signal. By way of example, and not limitation, communication media can include wired media such as a wired network or direct-wired connection, and wireless media such as acoustic, radio frequency (RF), infrared (IR) and other wireless media.

Computing device 400 can be implemented as a portion of a small-form factor portable, mobile, or embedded electronic device such as a cell phone, a personal data assistant (PDA), a personal media player device, a wireless web-watch device, a personal headset device, an application specific device, or a hybrid device that include any of the above functions. Computing device 400 can also be implemented as a personal computer including both laptop computer and non-laptop computer configurations.

Figure 5:
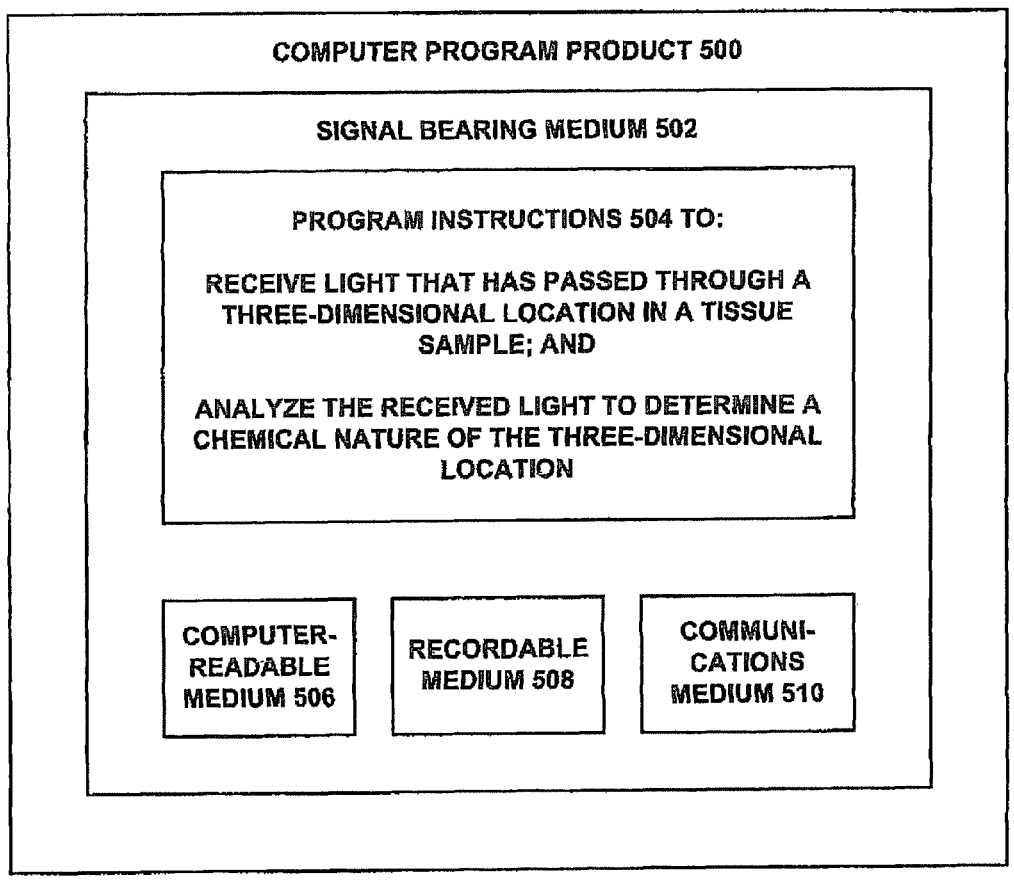
FIG. 5 is a schematic illustrating a partial view of an example computer program product, in accordance with an example embodiment.

FIG. 5 is a schematic illustrating a partial view of an example computer program product 500 that includes a computer program for executing a computer process on a computing device, arranged according to at least some embodiments presented herein. An illustrative embodiment of the example computer program product is provided using a signal bearing medium 502. Signal bearing medium 502 may include one or more program instructions 504 that, when executed by, for example, a processor, may provide the functionality described above with respect to FIGS. 1-4. Thus, for example, referring to FIG. 3, one or more features of steps 302 and/or 304 may be undertaken by one or more instructions associate with signal bearing medium 502.

The one or more instructions may be, for example, computer executable and/or logic implemented instructions. In some embodiments, the signal bearing medium 502 of one or more computer program products 500 include a computer readable medium 506, a recordable medium 508, and/or a communications medium 510. In some examples, a computing device such as computing device 400 of FIG. 4 may be configured to provide the various operations, function, or actions in response to program instructions 504 conveyed to computing device 400 by signal bearing medium 502.

In some implementations, signal bearing medium 502 may encompass a computer-readable medium 506, such as, but not limited to, a hard disk drive, a Compact Disc (CD), a Digital Video Disk (DVD), a digital tape, memory, etc. In some implementations, signal bearing medium 502 may encompass a recordable medium 508, such as, but not limited to, memory, read/write (R/W) CDs, R/W DVDs, etc. In some implementations, signal bearing medium 502 may encompass a communications medium 510, such as, but not limited to, a digital and/or an analog communication medium (e.g., a fiber optic cable, a waveguide, a wired communications link, a wireless communication link, etc.).

It should be understood that the methods, procedures, operations, devices, and systems illustrated in FIGS. 1-5 may be modified without departing from the spirit of the invention. For example, these methods, procedures, operations, devices, and systems may comprise more or fewer steps or components than appear herein, and these steps or components may be combined with one another, in part or in whole.

Furthermore, the present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or figures, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

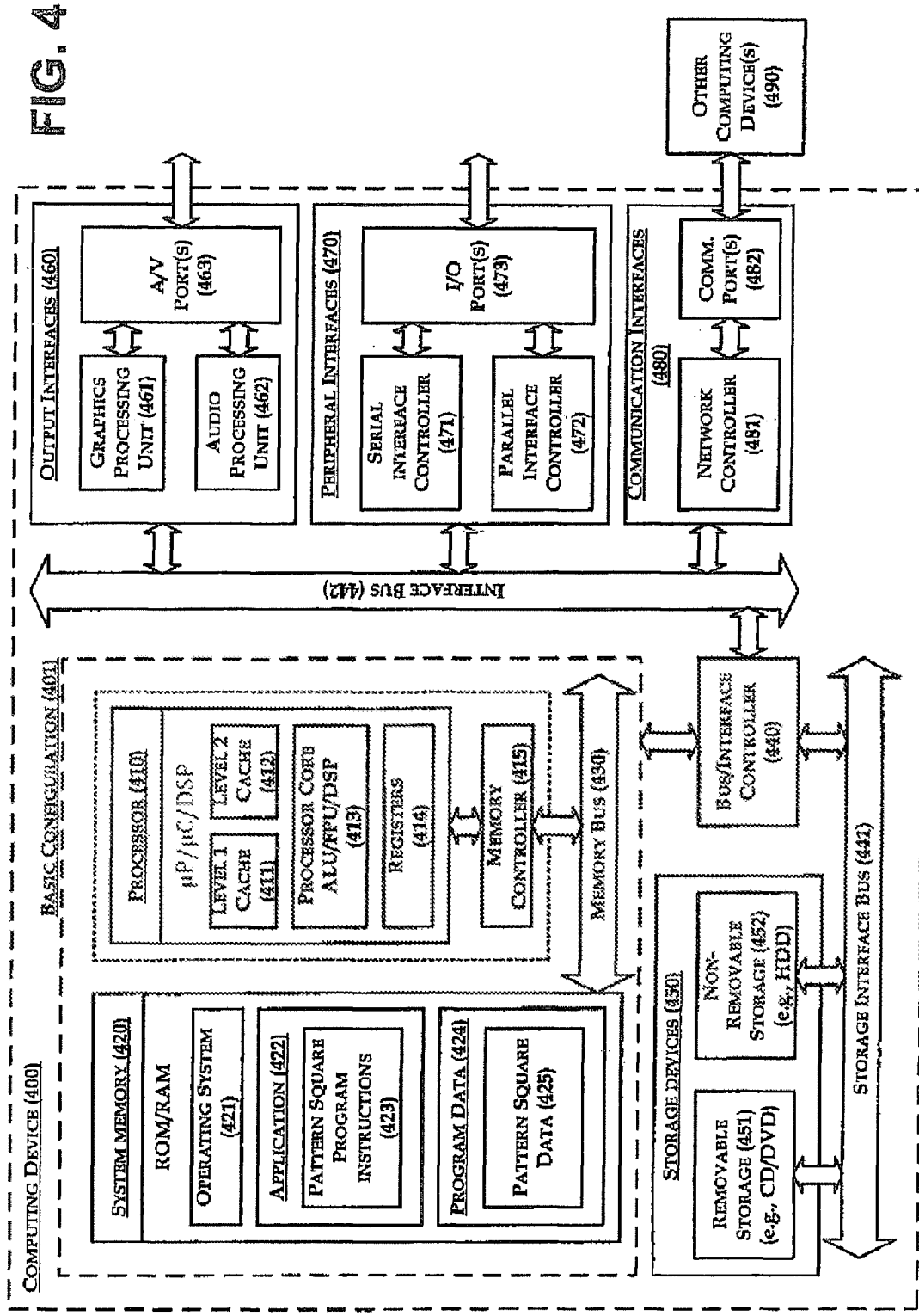

What is claimed is:

1. A device comprising:
   a light source configured to direct light at a three-dimensional location within a tissue sample, wherein a relative positioning of the light source and the tissue sample is adjustable to direct the light to additional three-dimensional locations in the tissue sample:
   a light receptor configured to receive light that has passed through the three-dimensional location in the tissue sample, wherein the light receptor comprises a lens configured to focus the received light;
   a collimator configured to parallelize the focused light; and
   an analyzer configured to receive the collimated light and to determine a chemical nature of the three-dimensional location based on one or more characteristics of the collimated light, wherein the chemical nature of the three-dimensional location includes a chemical structure of the tissue sample at the three-dimensional location.

2. The device of claim 1, wherein the light is substantially infrared or substantially near-infrared.

3. The device of claim 1, wherein the analyzer further comprises:
   a light disperser configured to receive the parallelized light and to diffuse the parallelized light into a plurality of spectral components; and
   a focal plane array configured to measure the respective intensity of each spectral component in the plurality.

4. The device of claim 1, wherein the light source is configured to provide substantially monochromatic light.

5. The device of claim 4, wherein the light source is adjustable to change the frequency of the substantially monochromatic light.

6. The device of claim 1, wherein the light source is configured to provide substantially polychromatic light.

7. The device of claim 1, wherein the relative positioning of the light source and the tissue sample is adjustable to change an angle of incidence of the light to the tissue sample.

8. The device of claim 1, wherein the relative positioning of the light source and the tissue sample is adjustable to change a focus of the light.

9. A method comprising:
   directing a light from a light source into a first three-dimensional location within a tissue sample, wherein a relative positioning of the light source and the tissue sample is adjustable to direct the light to additional three-dimensional locations in the tissue sample;

receiving light that has passed through the first three-dimensional location in the tissue sample;

focusing the received light; and analyzing the focused light to determine a first chemical nature of the first three-dimensional location, wherein the first chemical nature of the three-dimensional location includes a chemical structure of the tissue sample at the three-dimensional location.

10. The method of claim 9, wherein the light is substantially infrared.

11. The method of claim 9, wherein analyzing the received light comprises performing a spectral analysis of the received light.

12. The method of claim 9, wherein analyzing the received light comprises:

parallelizing the received light;

diffusing the parallelized light into a plurality of spectral components; and measuring the respective intensity of each spectral component in the plurality.

13. The method of claim 9, further comprising:

adjusting the relative positioning of the light source and the tissue sample to direct the light to a second three-dimensional location in the tissue sample; and analyzing the directed light that passes through the second three-dimensional location to determine a second chemical nature of the second three-dimensional location.

14. The method of claim 13, further comprising:

based on the first chemical nature and the second chemical nature, determining a morphology for at least part of the tissue sample.

15. The method of claim 14, wherein the tissue sample is derived from embryonic stem cells and the determined morphology comprises a tumor in the tissue sample.

16. The method of claim 9, wherein the light is substantially monochromatic or substantially polychromatic.

17. An article of manufacture including a non-transitory computer-readable medium, having stored thereon program instructions that, if executed by a computing device, cause the computing device to perform functions of:

directing a light from a light source into a first three-dimensional location within a tissue sample, wherein a relative positioning of the light source and the tissue sample is adjustable to direct the light to additional three-dimensional locations in the tissue sample;

receiving light that has passed through the three-dimensional location in the tissue sample;

focusing the received light; and analyzing the focused light to determine a chemical nature of the first three-dimensional location, wherein the chemical nature of the three-dimensional location includes a chemical structure of the tissue sample at the three-dimensional location.

18. The article of manufacture of claim 17, wherein the program instructions to analyze the received light comprise further program instructions for performing a Fourier transform or a wavelet transform of at least some of the received light.

* * * * *

UNITED STATES PATENT AND TRADEMARK OFFICE
CERTIFICATE OF CORRECTION

PATENT NO. : 9,063,074 B2
APPLICATION NO. : 13/202269
DATED : June 23, 2015
INVENTOR(S) : Paul It is certified that error appears in the above-identified patent and that said Letters Patent is hereby corrected as shown below:

Drawings:

In Fig. 4, Sheet 4 of 5, delete "uP/uC/DSP" and insert -- μP/μC/DSP --, therefor. (as shown on the attached)

Specification:

In Column 1, Lines 4-13, delete "BACKGROUND
Embryonic..........the tissue." and insert -- CROSS-REFERENCE TO RELATED APPLICATION
The present application claims priority to Indian patent application serial number 3168/DEL/2010, filed on Dec. 30, 2010, the entire contents of which are incorporated by reference. This present application is a U.S. National Phase Application pursuant to 35 U.S.C. §371 of International Application No. PCT/IB2011/000266 filed Feb. 14, 2011, the entire contents of which are incorporated by reference. --, therefor.

In Column 1, Lines 14-24, delete "CROSS-REFERENCE TO RELATED APPLICATION
The present application.......by reference." and insert -- BACKGROUND
Embryonic and adult stem cells have the potential to grow and diversify into various types of specialized cells. Thus, these cells may be able to be used for tissue re-growth or replacement. However, such engineered tissue often fails to develop properly in vitro or after being transplanted, as it may be subject to tumors, such as teratomas, that can grow encapsulated within the tissue. --, therefor.

In Column 5, Line 62, delete "Particular" and insert -- particular --, therefor.

In Column 6, Line 14, delete "a-light" and insert -- a light --, therefor.

In Column 7, Line 52, delete "controller 410." and insert -- controller 440. --, therefor.

In Column 7, Lines 56-57, delete "interfaces 460" and insert -- interfaces 470 --, therefor.

Signed and Sealed this
Tenth Day of November, 2015

Michelle K. Lee
*Director of the United States Patent and Trademark Office*